United States Patent [19]

Kiernan

[11] Patent Number: 4,779,593

[45] Date of Patent: Oct. 25, 1988

[54] MACHINE FOR PROVIDING ELECTROMAGNETIC PULSES FOR THERAPEUTIC PURPOSES

[76] Inventor: Kay Kiernan, Bluestone Clinic, 16 Harley House, Marylebone Road, London, NW1, England

[21] Appl. No.: 837,697

[22] Filed: Mar. 10, 1986

[51] Int. Cl.⁴ ............................................. A61N 1/40
[52] U.S. Cl. ................................... 128/422; 128/804
[58] Field of Search ................................ 128/422, 804

[56] References Cited

U.S. PATENT DOCUMENTS 3,800,802 4/1974 Berry et al. ......................... 128/422
3,978,864 9/1976 Smith .................................. 128/804
4,271,848 6/1981 Turner et al. ....................... 128/422

FOREIGN PATENT DOCUMENTS 591192 1/1978 U.S.S.R. ............................... 128/804
1496982 7/1976 United Kingdom ........... 128/419 D

OTHER PUBLICATIONS

"Wireless World", May, 1966, p. 234.

Primary Examiner—William E. Kamm
Attorney, Agent, or Firm—Roylance, Abrams, Berdo & Goodman

[57] ABSTRACT

A machine for providing electromagnetic pulses of a very high frequency for the therapeutic treatment of a body, which machine is portable and comprises a housing, a control panel, a treatment head holder, and at least two treatment heads which are of a different size to each other, the treatment heads being interchangeably engageable in the treatment head holder such that a different sized treatment head can be used for treating different parts of the body with electromagnetic pulses.

9 Claims, 7 Drawing Sheets

MACHINE FOR PROVIDING ELECTROMAGNETIC PULSES FOR THERAPEUTIC PURPOSES

This invention relates to a machine for providing electromagnetic pulses for therapeutic purposes. More specifically, this invention provides a machine for providing electromagnetic pulses of a very high frequency for the therapeutic treatment of a body.

Machines for providing electromagnetic pulses of a very high frequency for the therapeutic treatment of a body are known. Such machines comprise a housing for the electronic equipment for generating and controlling the electromagnetic output pulses of the machine, and a single treatment head which receives the pulses via coaxial cable, the treatment head being attached to the housing by means of an articulated arm. The existing machines are undesirably heavy and bulky and they are not readily portable. Furthermore, the single treatment head of the known machines is often too large for appropriately reaching some parts of the body such for example as under a person's neck, under a person's arm or under a person's toes.

It is an aim of the present invention to obviate or reduce the above mentioned problems.

Accordingly, this invention provides a machine for providing electromagnetic pulses of a very high frequency for the therapeutic treatment of a body, which machine comprises a housing, at least one carrying handle which is provided on the housing and which is for carrying the machine, a control panel which is mounted on the housing, at least two treatment heads which are of a different size to each other for holding against the body during the therapeutic treatment of the body, a connector portion on each of the treatment heads, a treatment head holder having detachable securing means for detachably securing the connector portion of a selected treatment head selected from at least two different sized treatment heads with the connector portion being received by the detachable securing means, transducer means which is provided in the housing and which is for producing direct current from a mains input a.c. voltage supply, cable means connected to the treatment head holder, a very high frequency pulse generating circuit which is provided in the housing and which is for delivering very high frequency pulses via the cable means and the treatment head holder to the treatment head in the treatment head holder, a pulse control and display circuit which is provided in the housing and which is electrically connected to the transducer means and to the very high frequency pulse generating circuit and which operates consequent upon receiving the direct current from the transducer means, control members which are provided on the control panel and which are electrically connected to and are for controlling the very high frequency pulse generating circuit and the pulse control and display circuit, and visual indicators which are provided on the control panel and which are electrically connected to the control members for enabling an operator of the machine to see which control members have been operated, and the machine being such that during use the treatment heads are only used one at a time so that different parts of the body requiring treatment can be treated with the treatment head that is of the appropriate size.

The electromagnetic pulses are of a very high frequency of the order of, for example, 27 MHz. The pulse repetition frequency may be such that there are 80 pulses per second up to 900 pulses per second, which represents an increased range of repetition frequencies compared with existing machines.

The machine may be one in which the machine includes an articulated arm having a plurality of hollow arm sections, in which the treatment head holder is positioned on the outermost end of the hollow arm section that is farthest from the housing, in which the cable means is a co-axial cable which extends through the hollow arm sections from the housing to the treatment head holder, and in which the said at least one carrying handle is a pair of the carrying handles, the pair of the carrying handles being formed as carrying handle recesses which are provided one in each of a pair of opposed sides of the housing.

There may be four of the hollow arm sections. The hollow arm sections may be rectangular hollow arm sections. Hollow arm sections of other cross sectional shapes may of course be employed.

Preferably, the machine is one in which the housing has an inclined front face, in which the inclined front face has a recess for receiving the control panel, and in which the control panel is an inclined control panel which is located in the recess such that the control panel is lower than the inclined front face and such that the control panel extends in a plane parallel to the inclined front face.

The treatment heads may be a push-in fit, a screw-in fit, or a bayonet fit in the treatment head holder. Preferably the machine is one in which the treatment head holder has an externally threaded tubular portion, in which the connector portion of each one of the treatment heads has an insert member for insertion into the tubular portion and a hand-operable captive locking member for screwing by hand on to the tubular portion when the insert member has been inserted into the tubular portion in order to lock the treatment head to the treatment head holder.

The pulse control and display circuit arrangement may provide a d.c. pulse output having a pulse repetition frequency, amplitude and duration dependent upon various values selected from the control panel. Preferably, the selected values are displayed by light emitting diode arrangements.

The pulse control and display circuit arrangement may include timing and counting means for measuring and displaying the exposure time of the body to the radiated electromagnetic pulses from the treatment head, and the total time for which the machine has been used. This enables servicing of the machine and calibration of various components to be carried out at proper predetermined time intervals.

The counting operation and the operation for producing the d.c. pulses having the requisite pulse repetition frequency may be controlled by oscillators, the output frequencies of which oscillators being independent of the frequency of the power supply to the machine. As a consequence, the calibration of various machine components and the indicated and the actual pulse repetition frequency of the machine output pulses, may be independent of the frequency of the power supply.

The machine may include output switching means, the machine then being one in which the d.c. pulses derived from the control and display circuit arrangement may be applied to the very high frequency pulse generating circuit when the output switching means is operated.

The machine may be one in which the very high frequency pulse generating circuit includes a crystal oscillator, the output from which crystal oscillator is controlled by the d.c. pulses applied to the very high frequency pulse generating circuit, and in which the controlled output in amplified by power amplifier means to produce pulses of the requisite power to give a desired body penetration before being fed to the treatment head in the treatment head holder consequent upon operation of switching means.

The machine of the present invention may be such that it can be operated from supplies of different voltages, for example 240 volts or 110 volts.

The machine may be such that the pulse repetition frequency of the output pulses remains steady, even if the supply frequency varies.

An embodiment of the invention will now be described solely by way of example and with reference to the accompanying drawings in which.

Figure 1:
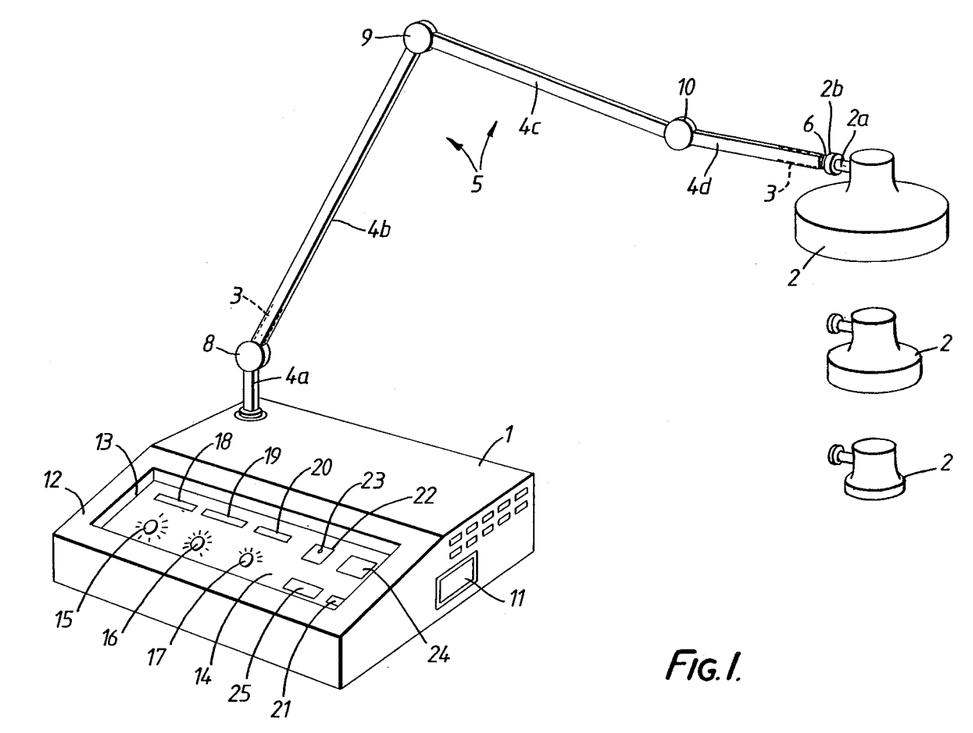
FIG. 1 is a perspective view of a complete machine according to the invention for producing intermittent or pulsed electromagnetic energy radiation at a very high frequency of, for example, the order of 27.125 MHz.

Referring to FIG. 1, there is shown a machine for providing electromagnetic pulses of a very high frequency for the therapeutic treatment of a body. The machine comprises a compact metal housing 1 which contains the electrical/electronic components for generating and controlling the requirements, the repetition frequency, amplitude and duration of pulses of a very high frequency. These pulses are typically of 27 MHz. The very high frequency pulses are delivered to a treatment head 2 via co-axial cable 3 which extends through hollow rectangular arm sections 4a, 4b, 4c, 4d of an articulated arm 5. The articulated arm 5 is removably attached to the housing 1. The arm section 4a can rotate about its axis relative to the housing 1 so that the arm 7 as a whole can swivel about the housing 1 for the general positioning of the treatment head 2. The treatment head 2 is detachably secured to the arm 7. More specifically, the arm section 4d is provided with an externally threaded hollow tube 6 which forms a treatment head holder 6. The treatment head holder 6 receives a connection portion of the treatment head 2 in the form of an arm 2a. The arm 2a is a push-in fit in the treatment head holder 6. The arm 2a is provided with a captive nut 2b which screws over the treatment head holder 6 to detachably secure the arm 2a in the treament head holder 6. The coaxial cable 3 terminates in an electrical connector socket (not shown) in the treatment head holder 6. The arm 2a has a complementary electrical connector pin (not shown), the two electrical connectors engaging when the arm 2a is pushed into the treatment head holder 6.

The treatment head 2 has a generally flat circular treatment surface 2b. Specific positioning of the treatment head 2 relative to a body part of a patient is provided for by means of adjustable friction joints, 8,9,10 of the articulated arm 5. Different treatment heads 2 as shown in FIG. 1 may be substituted for the treatment head 2. The two alternative treatment heads 2 shown in FIG. 1 are of the same general shape as the treatment head 2 in the treatment head holder 6 except that they are just of a smaller size. The smaller size is advantageous in reaching less accessible parts of the body. If desired the treatment heads 2 may be of a different shape than shown in FIG. 1 so that the treatment heads may be more cylindrical in shape or pointed or with inclined sides as may be desired.

The machine 2 is constructed of a size and weight that enables it readily to be portable. The machine housing 1 is formed with recessed side handles in opposing sides of the housing and one of these handles is shown as handle 11. The recessed handles facilitate the carrying of the machine.

As can be seen from FIG. 1, the machine housing 1 has an inclined front surface 12 which is provided with a recess 13. The recess 13 accommodates a machine control and display panel 14. This control and display panel has a layout which is shown in enlarged and greater detail in FIG. 2. Thus, as shown in both FIGS. 1 and 2, the control and display panel 14 comprises three rotatable control knobs 15,16 and 17 which control the repetition frequency (i.e. pulses per second), the amplitude (i.e. penetration of the radiated energy) and duration (i.e. pulse length), respectively, of the electromagnetic pulses of the machine. The control knobs 15,16 and 17 have apertaining light emitting diode displays 18,19 and 20 respectively associated therewith.

Figure 2:
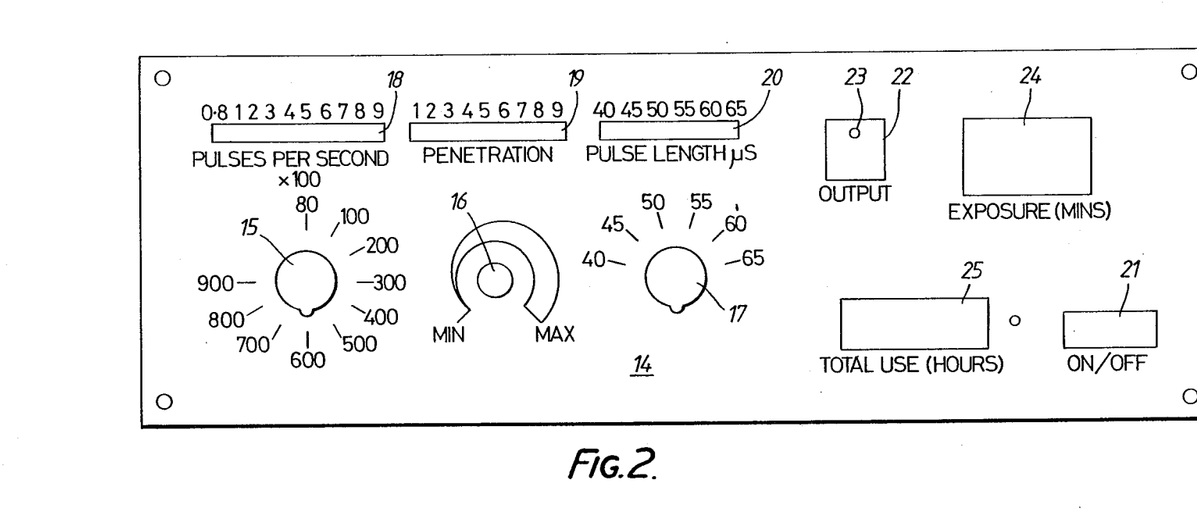
FIG. 2 is a front view of the control panel of the machine shown in FIG. 1.

The control panel 14 also includes an illuminated ON/OFF switch 21 which is a power supply ON/OFF switch. The control panel 14 also includes a machine output switch 22 which is for switching the machine on and off. The switch 22 has an integral warning light 23. When the machine output switch 22 is operated from the OFF to the ON position, an exposure timer operates to provide a light emitting diode digital display 24 in minutes of the time that the machine has been operating to expose a part of the body to the electromagnetic radiation. This exposure timer enables the machine operator to time the exposure of a patient to the radiated electromagnetic energy from the treatment head 2.

The machine also has a total use timer which cumulatively times the machine operation to give a digital light emitting diode display 25 of the total number of hours for which the machine has been operated. This facility enables servicing of the machine and/or calibration of components to be carried out when the machine has been used for a predetermined number of hours.

As will readily be appreciated from FIG. 1, the inclined position of the control panel 14 at the front of the machine enables the control knobs 15,16 and 17 to be operated with ease to provide the necessary knob settings for producing the requisite machine output, an indication of which requisite machine output can readily be seen from the light emitting diode display 18,19 and 20 on the inclined panel surface. The operative state of the ON/OFF switches 21,22, and also the exposure timer display 24 and the total use timer display 25 are also clearly visible to a machine operator from a position above the machine. Moreover, the control panel 14 is inset within the recess 13 and this serves to reduce the risk of damage to the control knobs 15,16 and 17 when the machine is being carried or is otherwise in transit.

Figure 3:
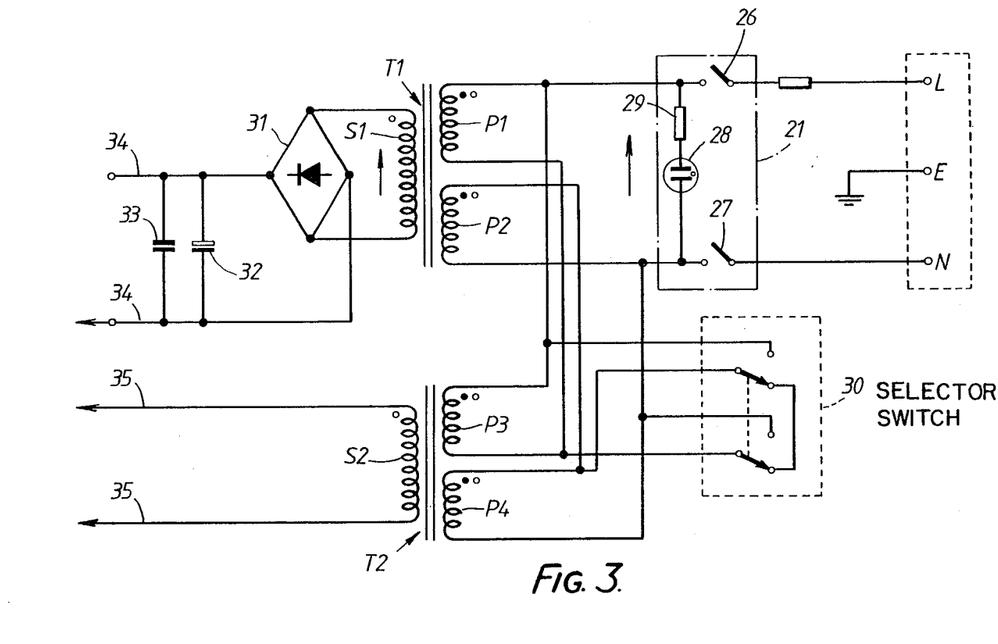
FIG. 3 is a circuit diagram of a power supply board for deriving from a mains supply of 240 volts or 110 volts (50 or 60 Hz respectively) specific d.c. and a.c. voltages of relatively low value required for the operation of the machine.

Referring now to FIG. 3, there is shown a circuit diagram of the power supply board for the machine. The power supply board comprises two transformers T1 and T2. The transformer T1 is of toroidal form and it comprises two primary windings P1, P2 and a secondary winding S1. The primary windings P1 and P2 of the transformer T1 are cross coupled with primary windings P3 and P4 of the transformer T2. The transformer T2 has a secondary winding S2.

The transformer primaries are arranged to be connected to a power supply through the illustrated ON/OFF power supply switch 21 which is also shown in FIG. 2. As shown in FIG. 3, the switch 21 comprises a pair of contacts 26,27, a neon device 28 and a resistance 29. The neon device 28 is fitted inside the switch 21. The resistance 29 is a current limiting resistor for the supply to the neon device 28. The resistance 29 is also fitted inside the switch 21. The machine is adapted to operate from a power supply of 240 volts or 110 volts a.c. at a frequency of 50 or 60 Hz. The voltage adaption is accomplished by appropriate operation of a mains voltage selector switch 30. The output from the secondary winding S1 of the transformer T1 is rectified by means of a full wave bridge rectifier 31 having smoothing capacitors 32, 33 connected across the output from the full wave bridge rectifier 31 to provide a smooth d.c. voltage output of 50 volts on lines 34. The secondary winding S2 of the transformer T2 provides an a.c. voltage output of 15 volts on lines 15.

Figure 4A:
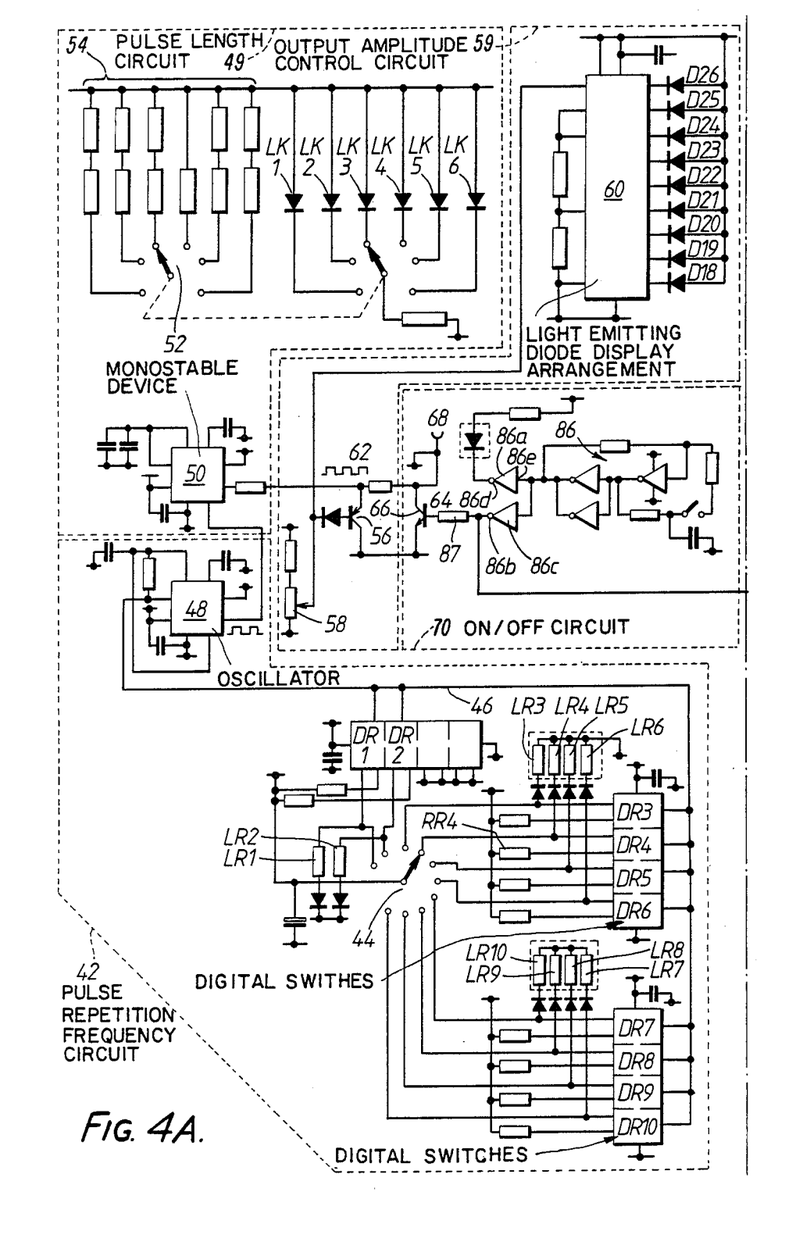
FIGS. 4A, 4B and 4C are a circuit diagram of the control and display arrangement of the machine shown in FIG. 1.
Figure 4B:
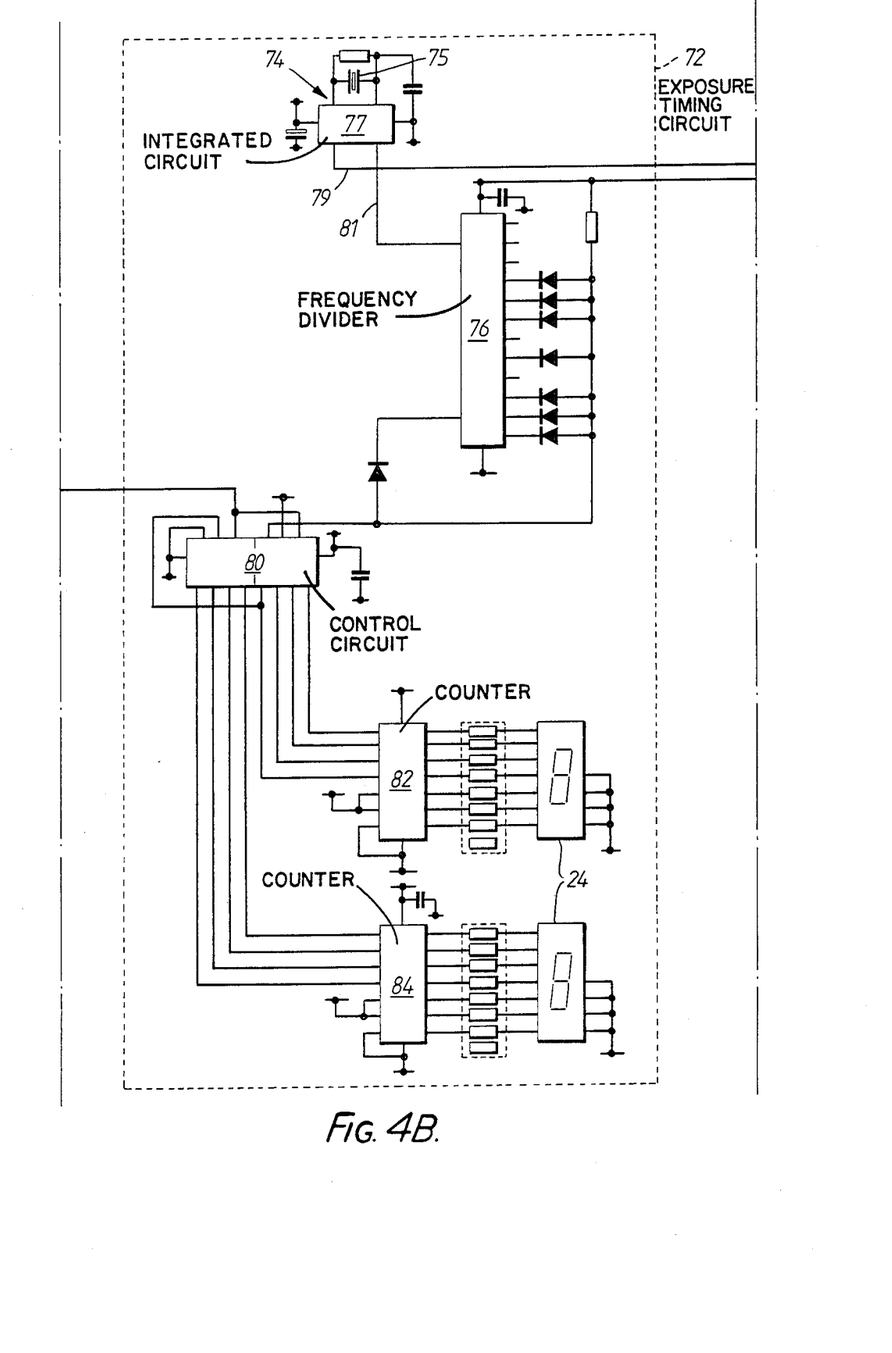
Figure 4C:
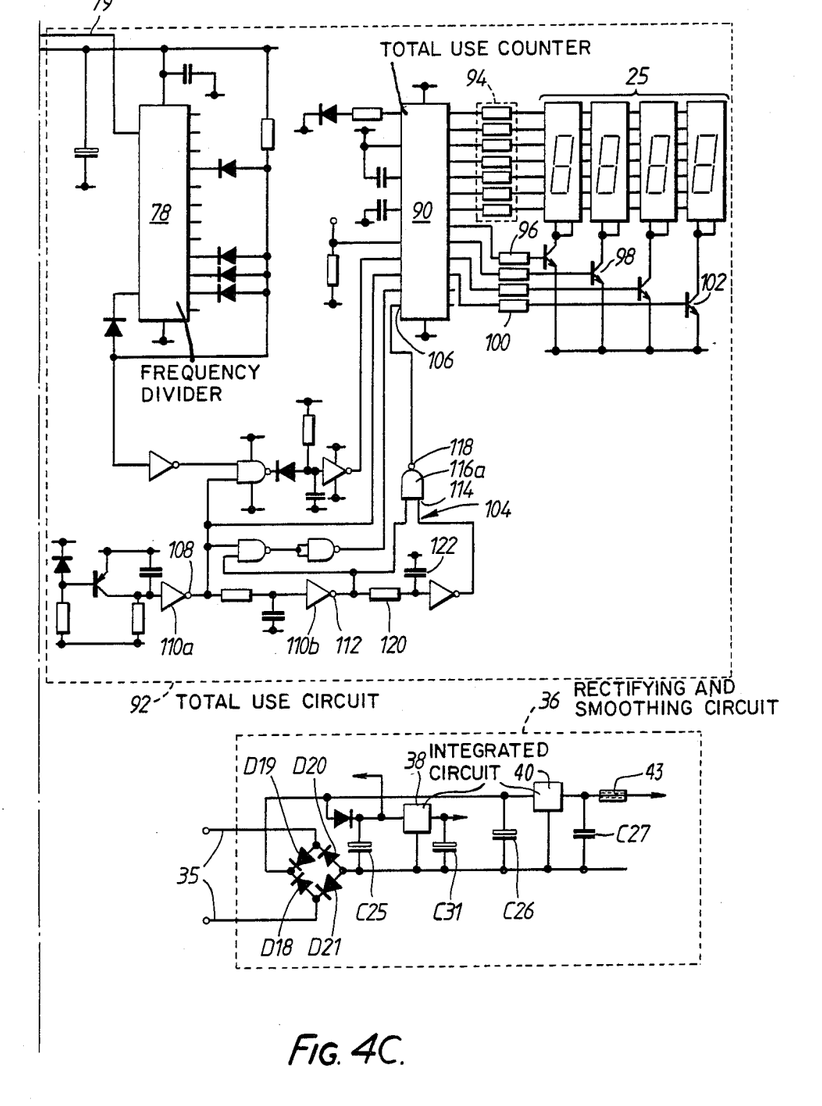
Figure 5:
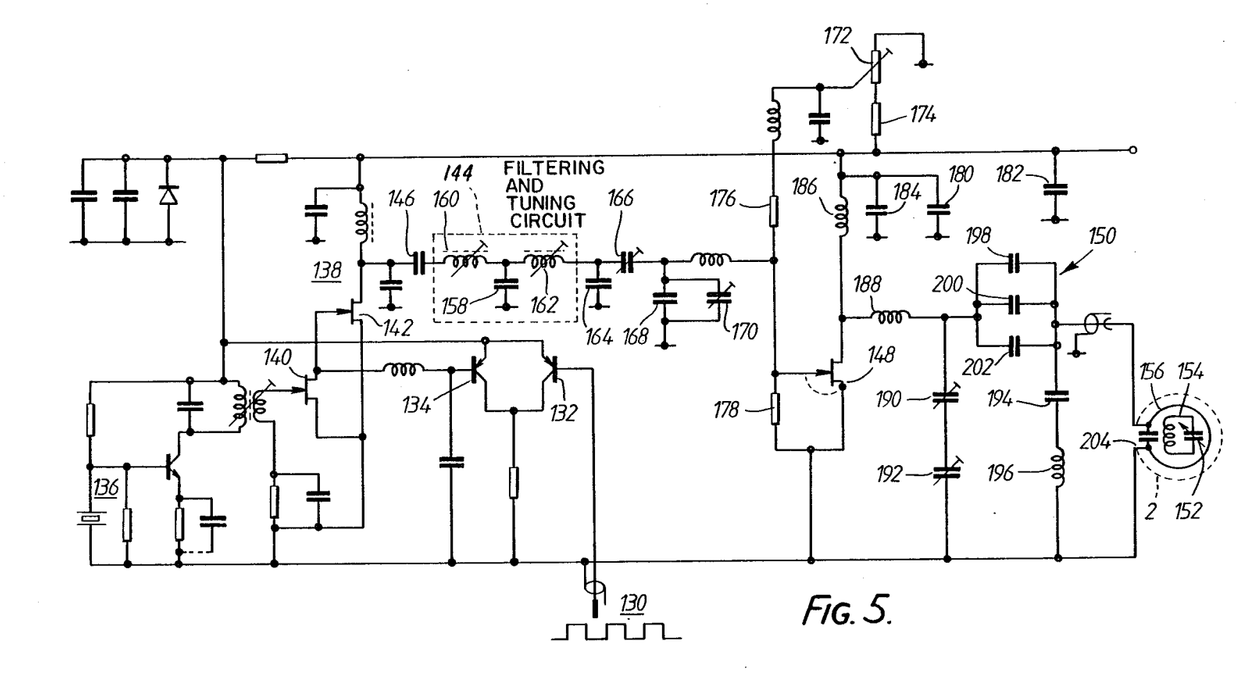
FIG. 5 is a circuit diagram of a circuit arrangement for generating at the treatment head of the machine pulses of very high frequency having the requisite repetition frequency, amplitude and duration.

The d.c. and the a.c. voltage outputs on lines 34, 35 are applied to the circuits shown in FIGS. 4 and 5.

Referring now to FIGS. 4A, 4B and 4C, there is shown the output control and display circuit arrangement of the machine. The 15 volts a.c. output on lines 35 from the FIG. 3 power supply board is applied to a rectifying and smoothing circuit shown in broken lines in FIG. 4C as rectifying and smoothing circuit 36. The rectifying and smoothing circuit 36 provides a 15 volts d.c. output which is applied to numerous points in the circuit arrangement illustrated in FIGS. 4A, 4B and 4C. Dealing more specifically with the operation of the rectifying and smoothing circuit 36, the 15 volts a.c. on lines 35 is bridge rectified by diodes D18–D21 and smoothed by capacitors C25,C25. This smoothed d.c. voltage is regulated to 12 volts d.c. by an integrated circuit 38 to provide a smoothed positive 12 volts d.c. on a capacitor C31. This smoothed positive 12 volts d.c. is regulated by an integrated circuit 40 to provide a smoothed positive 15 volts d.c. on capacitor C27. A ferrite bead 43 is provided to suppress radio frequency interference.

As previously described, the repetition frequency, amplitude and duration of the machine output pulses may be controlled by operation of the control knobs 15,16 and 17 as shown in FIGS. 1 and 2.

As regards the control of the repetition frequency of the output pulses, this is achieved by means of a ten position selector switch 44 which selectively applies a d.c. voltage of 15 volts to one of ten digital switches DR1–DR10 according to the repetition frequency selected. The pulse repetition frequency circuit is shown in dotted lines as block 42 in FIG. 4A. In the case of the embodiment illustrated in FIG. 4, repetition frequencies from which a selection may be made are 80, 100, 200, 300, 400, 500, 600, 700, 800 and 900 pulses per second.

The particular repetition frequency selected will be displayed by the energisation of one of the light emitting diode devices LR1–LR10 in the block 42. The light emitting diode devices LR1–LR10 are associated with appertaining digits marked on the control panel consequent upon the selector switch 44 extending an energising voltage (15 volts d.c.) to the light emitting diode device in question. This voltage is also applied by the selector switch 44 to the apertaining digital switch (for example DR4) which accordingly operates to extend an individual control signal via an appropriate resistor (for example resistor RR4) and a control lead 46 to an integrated circuit free-running oscillator 48, producing a pulse output. The repetition frequency of the oscillator pulse output (the time period between leading edges of successive pulses) is therefore adjusted in accordance with a control signal input applied to the oscillator 48 in dependence upon the position of the selector switch 44, which is turn is controlled by the control knob 15.

The pulse output derived from the oscillator 48 and having the selected repetition frequency, is applied to an integrated circuit monostable device 50. The pulse length circuit shown in dotted lines in FIG. 4A as block 49. The pulse output initiates the output pulse from the monostable device 50. The length of the pulse output from the output of the monostable device 50 is dependent upon the selected position of a two contact bank selector switch 52 and the value of a resistor from the group 54 selected by the switch 52. The length of the pulse from the output of the monostable device 50 controls the width of the output pulses from the monostable device 50. The selector switch 52 has six positions which appertain to pulse widths or lengths of 40, 45, 50, 55, 60 and 65 microseconds. The particular pulse length positions selected by the switch 52 will be indicated visually on the control panel 14 by the energisation of an appertaining light emitting diode from the group LK–LK6.

The monostable device 50 accordingly produces a d.c. pulse output having the requisite pulse repetition frequency and pulses of the requisite length.

For the purpose of providing the requisite degree of pulse penetration, a d.c. voltage input (e.g. 0–5 volts) to the base of a transistor 56 is controlled by means of a potentiometer 58. The potentiometer 58 is controlled by the control knob 16. The output amplitude control circuit is generally shown in dotted lines in FIG. 4A as block 59. The d.c. input voltage is also applied to a light emitting diode display arrangement 60, see also the light emitting diode display 19 in FIG. 2. The light emitting diode display 60 responds to provide a progressive display indication of from 1 to 9 to provide an indication of the depth of penetration of the machine output pulses.

The voltage output derived from the potentiometer 58 effectively serves to clamp the voltages at point 62 of the monostable device 50 output circuit, which in turn is connected to the emitter of the transistor 56 to a value between 0–5 volts so as to limit the amplitude of the output pulses from the monostable device 50 a value between 0 and 5 volts according to the setting of the potentiometer 58.

It may here be mentioned that after operation of the power supply ON/OFF switch 21, shown in FIG. 1 and before the machine output switch 22 shown in FIG. 2 is operated, point 64 in the output circuit of the monostable device 50 will be held at ground potential by the conduction of a transistor 66. This will prevent any output pulses reaching an output terminal 68 until the machine output switch is operated. The ON/OFF circuit is shown by dotted lines in FIG. 4A as block 70.

When the output switch is operated, d.c. pulses of appropriate repetition frequency, amplitude and pulse length of then applied to the output terminal 68.

Reference will now be made to the timing arrangement for providing the previously mentioned exposure and total use displays on the control panel 14. In FIG. 4B, the exposure timing circuit is shown by dotted lines as block 72. The basic timing means comprises a crystal oscillator 74 having a crystal 75 and an integrated circuit 77. The crystal oscillator 74 is started into operation when the power supply ON/OFF switch 21 is operated. The output from the crystal oscillator 74 is fed to two frequency dividers 76 and 78. The crystal 75 and the integrated circuit 77 function to give 50 Hz output on lines 79, 81 from the integrated circuit 77. The frequency divider 76 is configured to divide this signal by 3000, providing one pulse per minute into a counter control circuit 80. The counter control circuit 80 counts these pulses and applies counting pulses in sequence to a unit counter 82 and a tens counter 84. The control circuit 80 is arranged to be operated in response to a signal from the machine "output switch ON" circuit indicated generally at 86 in block 70. The control circuit 80 steps the counter 82 at minute intervals and the counter 84 at ten minute intervals, the total exposure time being displayed digitally by the display 24 on the control panel 14. The "output switch ON" switch is configured to be a bistable latch. The circuit at 86 powers on which the pins of the integrated circuit component 86a at logical high (1) and the pin 86b of the component 86c providing base current for transistor 66 via resistance 87. This effects switching of the transistor 66 on suppressing the output at switch 68 as previously described above. The logical high at pin 86d disables the output indicator warning light 23. Operating the output indicator warning light 23 causes the bi-stable latch to change state such that the pins 86d and 86e on the component 86a go to logic 0, enabling the output via the transistor 66, enabling the display to count via the integrated circuit 80, and enabling the output indicator warning light 23.

The output from the frequency divider 78 is fed to the total use counter 90. The total use circuit is indicated generally in FIG. 4C in broken lines as block 92. The total use counter 90 operates a four digit display 25 (see also FIG. 2) showing the total number of hours that the machine has been used. More specifically, the 50 Hz signal on line 79 is divided by the frequency divider 78 to give one pulse every 36 seconds or 0.01 hour. This pulse is counted by the total use counter 90 and the counter is configured to give outputs to a seven segment display via the component block 94 to show the total hours used as just mentioned. The total use counter 90 is configured to drive a multiplexed output display. The multiplexer digit drive is provided by resistance 96 and transistor 98, through to resistance 100 and transistor 102. The pulse input to the total use counter 90 is present all the time the equipment is powered on.

The total use circuit 92 includes a memory arrangement in which the total number of hours of machine use is stored when the machine is switched off after use. The transfer of the total hours use information to the counter memory is effected by a pulse output from a SAVE circuit 104 when the ON/OFF switch is operated. The memory for the total hours display is incorporated in the total use circuit 90. The value in the counter is locked in the memory when its save input pin 106 is taken to a logic "0". This occurs when power is switch off the equipment. The unregulated positive 12 volts supply collapses before the regulated positive 12 volt supply. The output from the pin 108 of the integrated circuit component 110a goes from 1 to 0, and the pin 112 from the integrated circuit component 110b goes from 0 to 1. Since pin 114 of integrated circuit component 116a is at 1, the pin 118 will go to 0, causing the count to be saved. The pin 114 will go to logic 0 after a delay caused by resistance 120 and capacitor 122, causing pin 118 to revert to logic 1, thus completing the save cycle.

Referring now to FIG. 5, the d.c. pulses from the output terminal 68 arrive at the input terminal 130. These pulses are of between 0–5 volts amplitude, dependent upon the requisite degree of penetration of the machine output pulses. The d.c. pulses arriving at the input terminal 130 cause two transistors 132,134 to conduct. During conduction of these two transistors 132,134, the output from a continuously running crystal oscillator 136 producing a signal frequency of 27.125 MHz is applied to the point 138 in the circuit via two conducting fieldeffect transistors 140, 142. Consequently, a series of pulses of frequency 27.125 MHz at a d.c. bias level occuring at point 138 are then fed through a filtering and tuning circuit indicating in broken lines in FIG. 5 as block 144. Capacitor 146 provides a d.c. block to the 50 volts. The filtered pulses are then applied to a main power amplifier 148 having an inductive load which causes the pulses of very high frequency to swing, thereby producing a swing of 50 volts each side of a 50 volts datum. If required, a further main amplifier may be embodied in the circuit, but in any event pulses from the amplifier or amplifiers are then filtered by a filtering circuit 150 before being applied to the treatment head 2. FIG. 5 illustrates how the treatment head 2 can be tuned for maximum output by adjustment of a variable capacitor 152 of the inductor/capacitor tuned circuit 14. The pulses of electromagnetic energy are radiated from a ring conductor 156.

In FIG. 5, the capacitor 158 in the filtering and tuning circuit 144 and the components 160, 162 provide a "T" filter tuned to 27.125 MHz to suppress side band signals.

The capacitors 164,166,168 and 170 provide signal amplitude control adjustment for the input of the main power amplifier 148.

The resistances 172,174,176 and 178 provide d.c. bias to the gate of the main power amplifier 148.

Capacitors 180 and 182 are power supply smoothing capacitors. Capacitor 184 is a decoupling capacitor to suppress high frequency spikes on the power supply.

Resistor 186 is a filter to prevent radio frequency from getting on to the supply.

Resistance 188 and capacitors 190,192 form a matching network to match the output impedance of the drain of the main power amplifier 148 to the load at the output terminal 68.

The capacitor 194 and the resistance 196 form a harmonic filter which has a high impedance of 27 MHz.

The capacitors 198, 200, 202 are blocking capacitors and they have a neglible effect at 27 MHz.

In the treatment head 2, the variable capacitor 152 may be adjusted for resonance at which maximum output is obtained from the treatment head 2. Preferably, the machine has two treatment heads 2 which are four inches (10.160 centimeters) and seven inches (17.780 centimeters) in diameter. The circuit for both of these treatment heads (and for any other treatment heads employed) is preferably the same, the difference between them being in the layout of the circuit board. The treatment head 2 is shown being supplied via co-axial cable 204 and this co-axial cable 204 preferably has a 50 ohms characteristic impedance.

As will be apparent from the foregoing, the repetition frequency of the machine pulse output is independent of the frequency of the supply, and consequently the frequency selected by the control knob 15 is the actual frequency of the electromagnetic pulse radiation. Moreover, the machine can be used on 240 volt or 110 volt power supplies, and at power supply frequencies of 50 or 60 Hz. The electrical/electronic circuitry of the machine will have an associated heat sink (not shown) for dissipating the heat generated during operation of the machine.

It is to be appreciated that the embodiment of the invention described above with reference to the accompanying drawings has been given by way of example only and that modifications may be effected. Thus, various of the illustrated circuit components may be rearranged. The coaxial cable 3 may terminate in an electrical connector pin, in which case the arm 2a may terminate in a complementary electrical connector socket.

I claim:

1. A machine for providing electromagnetic pulses a very high frequency for the therapeutic treatment of a body, which machine comprises a housing, at least one carrying handle which is provided on the housing and which is for carrying the machine, a control panel which is mounted on the housing, a connector portion on each of the treatment heads, a treatment head holder having detachable securing means for detachably securing the connector portions of a selected body engaging treatment head selected from at least two different sized body engaging treatment heads with the connector portion being received by the detachable securing means, transducer means which is provided in the housing and which is for producing direct current from a mains input a.c. voltage supply, cable means connected to the treatment head holder, a very high frequency pulse generating circuit which is provided in the housing and which is for delivering very high frequency pulses via the cable means and the treatment head holder to the treatment head in the treatment head holder, a pulse control and display circuit which is provided in the housing and which is electrically connected to the transducer means and to the very high frequency pulse generating circuit and which operates consequent upon receiving the direct current from the transducer means, control members which are provided on the control panel and which are electrically connected to and are for controlling the very high frequency pulse generating circuit and the pulse control and display circuit, and visual indicators which are provided on the control panel and which are electrically connected to the control members for enabling an operator of the machine to see which control members have been operated, and the machine being such that during use the treatment heads are only used one at a time so that different parts of the body requiring treatment can be treated with the treatment head that is of the appropriate size.

2. A machine according to claim 1 in which the machine includes an articulated arm having a plurality of hollow arm sections, in which the treatment head holder is positioned on the outermost end of the hollow arm section that is farthest from the housing, in which the cable means is a co-axial cable which extends through the hollow arm sections from the housing to the treatment head holder, and in which the said at least one carrying handle is a pair of carrying handles, the pair of the carrying handles being formed as carrying handle recesses which are provided one in each of a pair of opposed sides of the housing.

3. A machine according to claim 2 in which the treatment head holder has an externally threaded tubular portion, in which the connector portion of each one of the treatment heads has an insert member for insertion into the tubular portion and a hand-operable captive locking member for screwing by hand on to the tubular portion when the insert member has been inserted into the tubular portion in order to lock the treatment head to the treatment head holder.

4. A machine according to claim 1 in which the housing has an inclined front face, in which the inclined front face has a recess for receiving the control panel, and in which the control panel is an inclined control panel which is located in the recess such that the control panel is lower than the inclined front face and such that the control panel extends in a plane parallel to the inclined front face.

5. A machine according to claim 4 in which the pulse control and display circuit includes timing and counting means for measuring the exposure time of the body to the electromagnetic pulses coming from the treatment head, and the total time for which the machine has been used, and in which the control and display circuit includes display means for displaying the measured exposure time and the measured total time.

6. A machine according to claim 5 and including oscillators for controlling both the counting means and the very high frequency pulse generating circuit, the oscillators including means producing output frequencies which are independent of the frequency of the power supply to the machine.

7. A machine according to claim 6 in which the very high frequency pulse generating circuit includes pwoer amplifier means for producing pulses of a requisite power to give a desired body penetration.

8. A machine according to claim 7 in which the control members on the control panel include a first control member having means controlling the repetition frequency of the electromagnetic pulses, a second control member having means for controlling the amplitude of the electromagnetic pulses, and a third control member having means controlling the duration of the electromagnetic pulses.

9. A machine according to claim 8 in which the first control member is a ten position selector switch having means for providing repetition frequencies of 80, 100, 200, 300, 400, 500, 600, 700, 800 and 900 pulses per second, and in which the machine includes a plurality of light emitting diode devices and means for causing the particular repetition frequency selected by the selector switch to be displayed by the energisation of one of the light emitting diode devices, there being a separate one of the light emitting diode devices for each of the repetition frequencies.

* * * * *